United States Patent
Miller et al.

(10) Patent No.: US 7,927,334 B2
(45) Date of Patent: Apr. 19, 2011

(54) MULTI-DIRECTIONAL ROD REDUCER INSTRUMENT AND METHOD

(75) Inventors: Keith E. Miller, Germantown, TN (US); James L. Cline, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1153 days.

(21) Appl. No.: 11/402,523

(22) Filed: Apr. 11, 2006

(65) Prior Publication Data

US 2007/0270867 A1    Nov. 22, 2007

(51) Int. Cl.
*A61B 17/70* (2006.01)
(52) U.S. Cl. .................................. 606/86 A
(58) Field of Classification Search ............. 606/86 A
See application file for complete search history.

(56) References Cited

U.S. PATENT DOCUMENTS

| | | | |
|---|---|---|---|
| 3,844,291 A | 10/1974 | Moen | |
| 4,271,836 A * | 6/1981 | Bacal et al. ............. | 606/86 A |
| 5,113,685 A | 5/1992 | Asher et al. | |
| 5,314,431 A | 5/1994 | Graziano | |
| 5,330,472 A | 7/1994 | Metz-Stavenhagen | |
| 5,389,099 A | 2/1995 | Hartmeister et al. | |
| 5,449,361 A | 9/1995 | Preissman | |
| 5,458,608 A | 10/1995 | Wortrich | |
| 5,466,243 A | 11/1995 | Schmieding et al. | |
| 5,616,143 A | 4/1997 | Schlapfer et al. | |
| 5,720,751 A | 2/1998 | Jackson | |
| 5,782,830 A | 7/1998 | Farris | |
| 5,899,901 A | 5/1999 | Middleton | |
| 5,910,141 A | 6/1999 | Morrison et al. | |
| 5,944,720 A | 8/1999 | Lipton | |
| 6,036,692 A | 3/2000 | Burel et al. | |
| 6,042,582 A | 3/2000 | Ray | |
| 6,063,088 A | 5/2000 | Winslow | |
| 6,440,133 B1 | 8/2002 | Beale et al. | |
| 6,648,888 B1 | 11/2003 | Shluzas | |
| 6,660,006 B2 | 12/2003 | Markworth et al. | |
| 6,746,449 B2 | 6/2004 | Jones et al. | |
| 2002/0095153 A1 | 7/2002 | Jones et al. | |
| 2003/0028195 A1 | 2/2003 | Bette | |
| 2006/0009775 A1 | 1/2006 | Dec et al. | |

FOREIGN PATENT DOCUMENTS

WO    WO 2005/006948    1/2005

* cited by examiner

*Primary Examiner* — Eduardo C Robert
*Assistant Examiner* — Julianna N Harvey

(57) ABSTRACT

A surgical reducing instrument is used to position an elongated implant element in a desired position relative to one or more of the bone anchors of a spinal implant system. The reducing instrument includes a mounting member that is mounted to the anchor and extends along a first longitudinal axis and an implant reducing member pivotally linked to the mounting member that extends along a second longitudinal axis that is offset from and variably positionable relative to the first longitudinal axis about a pivot axis. The reducing member contacts the implant element and includes a manipulation portion to move the implant element along the second longitudinal axis and can maintain contact to move the implant element toward the bone anchor when the reducing member is pivoted relative to the mounting member about the pivot axis.

20 Claims, 5 Drawing Sheets

MULTI-DIRECTIONAL ROD REDUCER INSTRUMENT AND METHOD

BACKGROUND

The present application relates to a surgical instrument and a manner of using the same, and more particularly, but not exclusively, relates to the reduction of spinal rods or other elongated implant components to one or more bone anchors in an orthopedic construct for treatment of a spinal deformity.

The use of surgical instruments to place components in orthopedic constructs has become commonplace. In particular, spinal implant systems frequently include several bone anchors and an interconnecting rod that is shaped to provide a desired spinal curvature. Typically, the bone anchors are implanted first and the rod is then fixed to the bone anchors in succession. As this procedure progresses, some degree of force may need to be applied to reduce the distance between the rod and the next anchor to be connected to it. Accordingly, various instruments have been described to facilitate such rod reduction. In this arena, the desire persists for better rod reducing capability. Thus, there is a need for additional contributions in this area of technology.

SUMMARY

One embodiment of the present application is a unique surgical instrument. Other embodiments include unique methods, systems, devices, instrumentation, kits, and apparatus involving an implant reduction instrument.

According to one aspect, a surgical reducing instrument is used to position an elongated implant element in a desired position relative to one or more of the bone anchors of a spinal implant system. The reducing instrument includes a mounting member that is mounted to the anchor and extends along a first longitudinal axis and an implant reducing member pivotally linked to the mounting member that extends along a second longitudinal axis that is offset from and variably positionable relative to the first longitudinal axis about a pivot axis. The reducing member contacts the implant element and includes a manipulation portion to move the implant element along the second longitudinal axis and can maintain contact to move the implant element toward the bone anchor when the reducing member is pivoted relative to the mounting member about the pivot axis.

According to another aspect, a surgical instrument to position an implant element relative to a bone anchor of a spinal implant system includes an elongated extension, a mounting member, a reducing member and a lateral displacement member. The extension includes a distal end removably engageable to the bone anchor and extends along a first longitudinal axis from the anchor a proximal end. The mounting member is removably mountable to the proximal end of the extension along the first longitudinal axis. The reducing member extends along a second longitudinal axis and is pivotally linked about a pivot axis to the mounting member in side-by-side relation therewith. The reducing member includes at least one leg movable distally along the second longitudinal axis for positioning in contact with the implant element. The lateral displacement member is engaged to one of the mounting member and the reducing member and is positionable in contact with a proximal portion of the other of the mounting member and the reducing member. The lateral displacement member is operable to move the proximal portion of the reducing member away from the mounting member about the pivot axis to move a distal end of the at least one leg toward the distal end of the extension and thus position the implant element in a location more proximate the bone anchor.

In another aspect, a surgical instrument is operable to position implants relative to a bone anchor of a spinal implant system. The instrument includes an elongated implant element, a mounting member removably mountable to the bone anchor along a first longitudinal axis, and a reducing member. The mounting member includes at least one linking arm extending therefrom in an oblique orientation to the first longitudinal axis to a pivot end. The reducing member extends along a second longitudinal axis and includes a housing portion and a manipulation portion mounted to and movable relative to the housing portion. The housing portion is pivotally coupled to the pivot end of the linking arm about a pivot axis. The manipulation portion includes at least one distally extending leg contacting the implant element. The at least one leg is movable distally relative to the housing portion along the second longitudinal axis for moving the implant element along the second longitudinal axis and the reducing member is pivotal relative to the mounting member about the pivot axis to change an orientation of the first and second longitudinal axes relative to one another and move the implant element transversely to the first longitudinal axis.

According to another aspect, a method for positioning an implant element into a bone anchor, comprises: engaging the bone anchor to a vertebra of a spinal column; positioning the implant element adjacent the bone anchor; mounting a mounting member to the bone anchor with the mounting member extending proximally from the bone anchor along a first longitudinal axis; contacting the implant element with a reducing member, the reducing member being pivotally linked to the mounting member about a pivot axis and extending along a second longitudinal axis in generally side-by-side relation with the first longitudinal axis; distally displacing the implant element relative to the bone anchor by moving at least one portion of the reducing member along the second longitudinal axis; and laterally displacing the implant element toward the bone anchor by pivoting the reducing member about the pivot axis toward the bone anchor while maintaining contact with the implant element.

Further embodiments, forms, features, aspects, benefits, objects, and advantages of the present application shall become apparent from the detailed description and figures provided herewith.

DETAILED DESCRIPTION OF REPRESENTATIVE EMBODIMENTS

Figure 1:
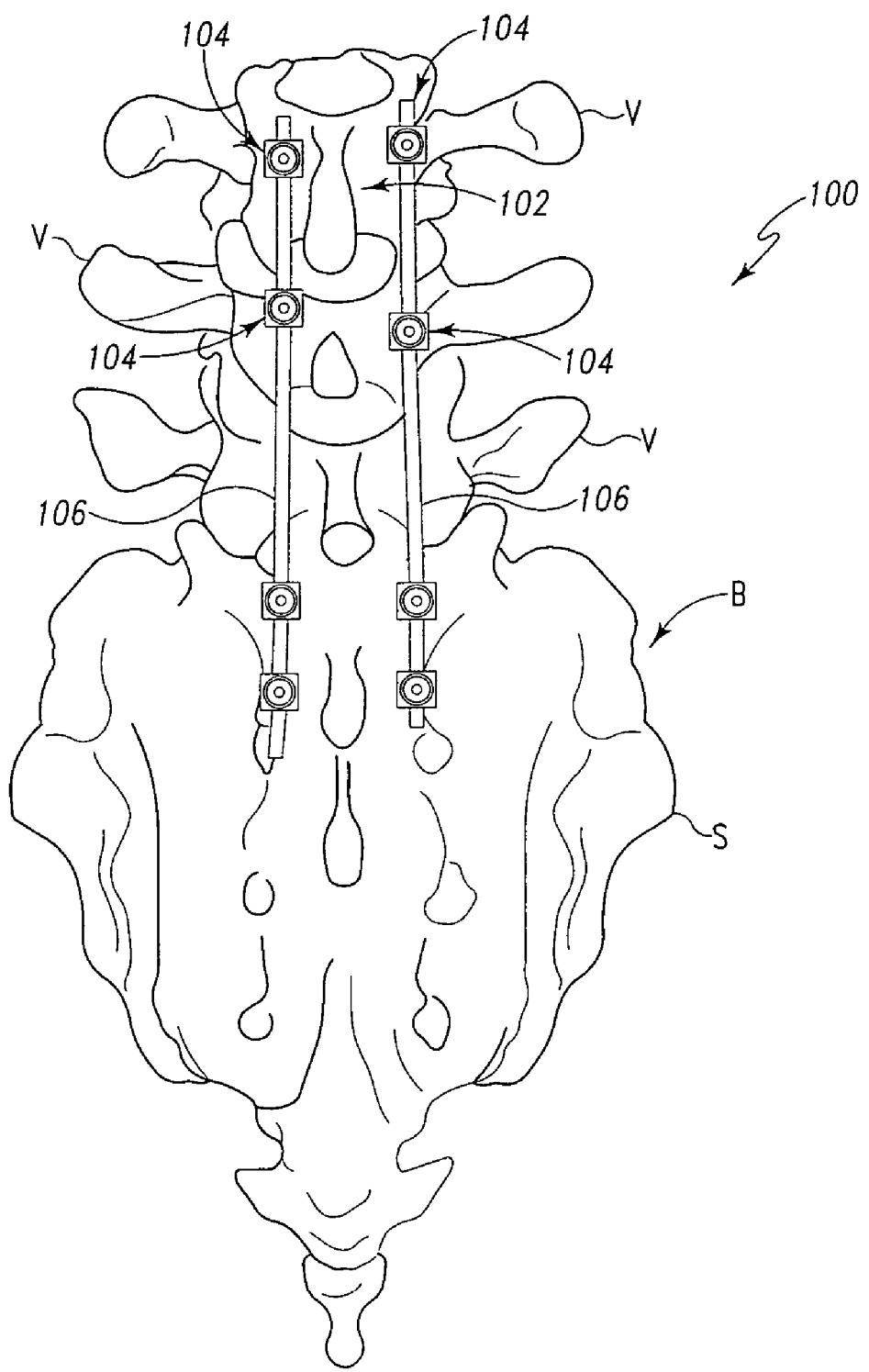
FIG. 1 is a posterior elevation view of a spinal column segment and spinal implant system.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates a posterior spinal implant system 100 located along a spinal column of a patient. More specifically, implant system 100 can be affixed to bones B of the spinal column segment 102 from a posterior approach. Bones B include the sacrum S and several vertebrae V. Implant system 100 generally includes several bone anchors 104 and elongated implant elements 106 structured to selectively interconnect with bone anchors 104. Implant elements 106 may be a spinal rod, plate, bar, or other elongated element having a length to extend between at least two vertebrae. Implant element 106 may be solid or hollow along some or all of its length and/or may be of homogenous or heterogeneous composition. In implant system 100, bone anchors 104 are affixed to various locations of the spinal column 102 and interconnected with implant elements 106. Spinal implant system 100 may be used for, but is not limited to, treatment of degenerative spondylolisthesis, fracture, dislocation, scoliosis, kyphosis, spinal tumor, and/or a failed previous fusion.

Figure 2:
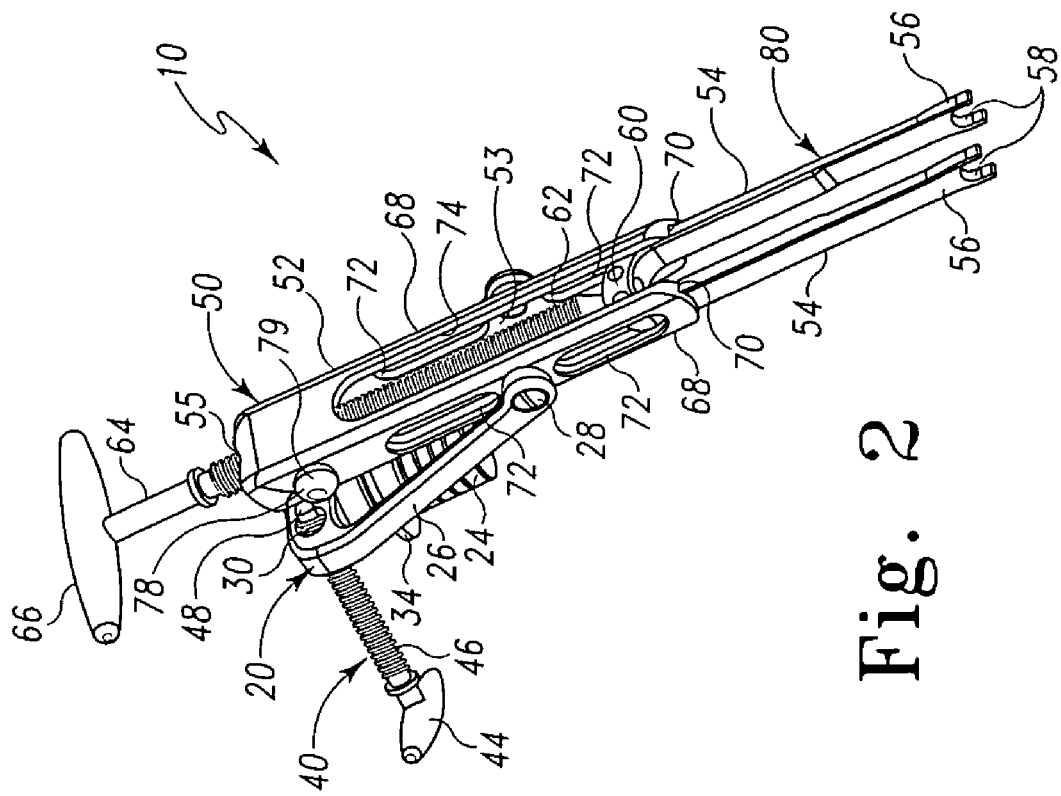
FIG. 2 is a perspective view of one embodiment surgical reduction instrument for positioning an implant element in a desired position relative to an anchor.
Figure 3:
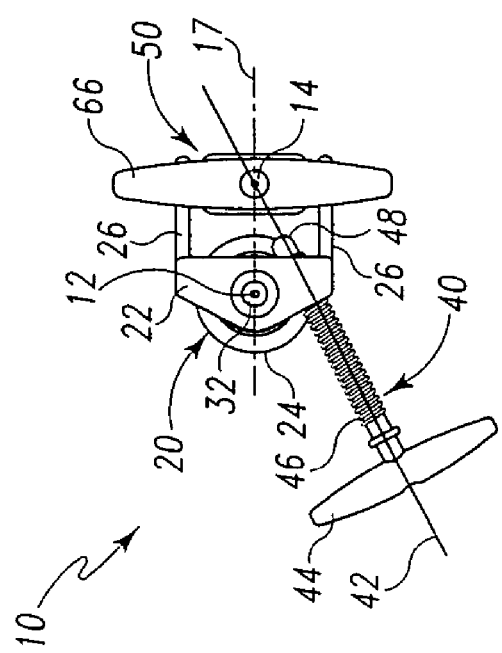
FIG. 3 is a top plan view of the surgical reduction instrument of FIG. 2.
Figure 4:
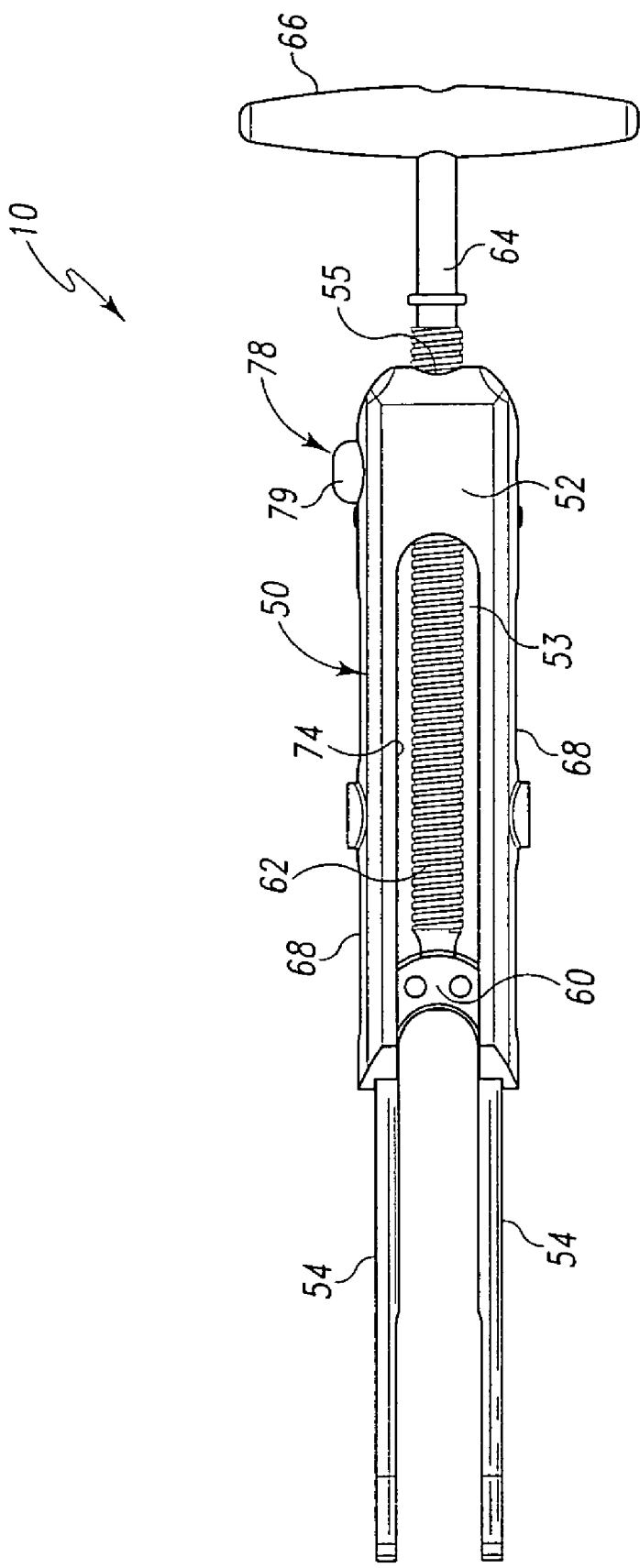
FIG. 4 is a side plan view of the surgical reduction instrument of FIG. 2.

A surgical reducing instrument 10 used to position implant element 106 in a desired position relative to one or more of the bone anchors 104 of spinal implant system 100 is shown in FIGS. 2-4. Reducing instrument 10 includes a mounting member 20 that extends along a first longitudinal axis 12 and an implant reducing member 50 that extends along a second longitudinal axis 14 that is offset from and variably positionable relative to longitudinal axis 12. Longitudinal axes 12 and 14 can be arranged relative to one another so that each lies in a single plane extending between axes 12 and 14, although such an arrangement is not required.

As further shown in FIGS. 5-8, mounting member 20 can be mounted to an extension 130 extending proximally from bone anchor 104 along first longitudinal axis 12, and implant reducing member 50 can be engaged to an implant element 106 that is offset from bone anchor 104. Implant reducing member 50 includes at least a portion that is movable relative to bone anchor 104 along longitudinal axis 14 to move implant element 106 distally relative to bone anchor 104 to align implant element 106 with bone anchor 104. Implant reducing member 50 is further movable relative to bone anchor 104 and mounting member 20 about a pivot axis 16 to orient second longitudinal axis 14 in the position indicated by axis 14' and in an oblique orientation to first longitudinal axis 12. Such movement of reducing member 50 moves implant element 106 along an arc or transverse path 18 that is transverse to first longitudinal axis 12 and into a receiver of bone anchor 104 where implant element 106 may be secured therein.

Referring back to FIGS. 2-4, reducing instrument 10 will be discussed in further detail. Mounting member 20 includes a head portion 22 along a proximal end thereof and an extension 24 extending distally from head portion 22 along longitudinal axis 12. Mounting member 20 includes a central passage 32 extending distally and proximally through head portion 22 and extension 24 along first longitudinal axis 12. At least a portion of central passage 32 can be sized for positioning about a proximal end of extension 130 to locate reducing instrument 10 in position relative to bone anchor 104. Extension 24 can further include a radial flange to facilitate grasping and manipulation of mounting member 20 and extension 24.

Mounting member 20 is linked to reducing member 50 with a pair of linking arms 26 that extend distally from head portion 22 and are pivotally coupled to opposite sides of a housing portion 52 of reducing member 50 with mounting anchors 28. Linking arms 26 can extend in an oblique orientation to longitudinal axis 12, as shown more clearly in FIG. 6, so that reducing member 50 and mounting member 20 can be oriented with axes 12 and 14 in offset and parallel relation to one another. Linking arms 26 can be integrally formed with head portion 22.

Reducing member 50 includes a housing portion 52 having a box-like and elongated configuration along longitudinal axis 14. Linking arms 26 are pivotally coupled to opposite sides of housing portion 52. Housing portion 52 includes an internal cavity 53 having a proximal opening 55 in communication with cavity 53. Housing portion 52 further includes a pair of rails 68 extending along a distal portion thereof that define a distally opening slot 74 therebetween that is in communication with cavity 53. Rails 68 further include windows 72 extending therethrough in communication with cavity 53. Rails 68 also include grooves 70 extending along at least distal portions thereof. Grooves 70 are formed along the respective inner sides of rails 68 and are oriented so that they are facing one another.

Reducing member 50 further includes a manipulation portion 80 engaged with housing portion 52 and movable relative thereto to guide implant element 106 in contact therewith toward bone anchor 104. Manipulation portion 80 includes an elongated drive member 62 extending along longitudinal axis 14 with a shaft 64 extending between a distal connector 60 and a proximal handle 66. Shaft 64 can include an outer thread profile extending therealong within housing portion 52. First and second legs 54 extend distally from the U-shaped connector 60 along longitudinal axis 14 to respective distal ends 56. Distal ends 56 each include a distally oriented concave engaging surface 58 configured to extend at least partially about the implant element 106 to couple or contact implant element 106 with manipulation portion 80. Engaging surfaces 58 are oriented to extend toward bone anchor 104 so that an elongated implant element 106 can be positioned to extend between legs 54 transversely to longitudinal axis 14.

Legs 54 can be separated from one another by a space to allow at least the distal ends 56 of legs 54 to be received on opposite sides of bone anchor 104 and facilitate positioning of implant element 106 into bone anchor 104 by manipulating the location of legs 54 relative to bone anchor 104. Legs 54 can be rigidly connected together with connector 60 to facilitate application of manipulation forces through the legs 54 to the implant element 106 in contact therewith. In addition, legs 54 can be received in respective ones of the grooves 70 along rails 68 to provide further stability to legs 54 as implant manipulation forces are applied through legs 54 to implant 106.

Shaft 64 extends proximally from housing portion 52 to handle 66. Handle 66 can be a T-handle transversely oriented to shaft 64, although other handle configurations are contemplated. Handle 66 can be permanently affixed or removable from shaft 64. Other embodiments contemplate that shaft 64 can include a proximal end configured to engage a mechanical drive instrument. Shaft 64 can include a radially extending flange 65 proximal of housing portion 52 that contacts the proximal end of housing portion 52 about proximal opening 55 to limit distal displacement of manipulation portion 80 relative to housing portion 52. The distal end of shaft 64 is captured in connector 60 and rotatable relative thereto so that rotation and distal advancement of shaft 64 translates into axial and non-rotational distal displacement of legs 54 along rails 68.

In one embodiment, reducing member 50 can further include a quick-release mechanism 78 mounted to housing portion 52 that is normally biased into engagement with manipulation portion 80. Specifically, shaft 64 can be threadingly engaged to a retaining member (not shown) in housing portion 52 that is coupled with button portion 79 protruding from housing portion 52. Button portion 79 can be normally biased to protrude from housing portion 52 and so that the retaining member is normally engaged with shaft 64. When button 79 is depressed into housing portion 52, the retaining member releases shaft 64 so that manipulation portion 80 is free to slide proximally and distally along longitudinal axis 14 relative to housing portion 52. In this embodiment, the user has the option to quickly distally displace manipulation portion 80 relative to housing portion 52 without rotating shaft 64 with handle 66. In other embodiments, a quick-release mechanism is not provided and shaft 64 is threadingly engaged to housing portion 52, such as within proximal opening 55.

In order to facilitate and provide a mechanical advantage in moving reducing member 50 about pivot axis 16, and thus in moving implant element 106 along an arc defined by a radius extending through pivot axis 16, a lateral displacement member 40 is provided. Lateral displacement member 40 includes an elongated shaft 46 extending along longitudinal axis 42 to an outer handle 44. Longitudinal axis 42 can be obliquely oriented to a plane 17 including first and second longitudinal axes 12 and 14 (FIG. 3) so that lateral displacement member 40 does not obstruct passage 32. Handle 44 can be a T-handle transversely oriented to shaft 46, although other handle configurations are contemplated. Handle 44 can be permanently affixed or removable from shaft 46. Other embodiments contemplate that shaft 46 can include an outer end configured to engage a mechanical drive instrument.

Shaft 46 includes a contact end 48 opposite handle 44 that is positioned in contact with an outer surface of housing portion 52 adjacent the proximal end of housing portion 52 proximally of pivot axis 16. Shaft 46 is threadingly engaged through a bore 30 in proximal head portion 22 of mounting member 20 that extends along axis 42. Contact end 48 is movable along axis 42 in the direction of arrow 43 (FIG. 6) into contact with the proximal portion of housing portion 52, and is further movable along axis 42 to pivot reducing member 50 about pivot axis 16. This in turn moves implant element 106 along an arc or path 18 toward bone anchor 104. Reducing member 50 can be pivoted about axis 16 in the opposite direction when contact end 48 is displaced from the proximal portion thereof by threading shaft 46 in bore 30 in the opposite direction of arrow 43 along axis 42.

In another embodiment, lateral displacement member 40 can be mounted to reducing member 50 by, for example, shaft 46 threadingly engaging a bore in the proximal portion of reducing member 50. Contact end 48 can contact a proximal end of mounting member 20, and is operable by rotation of shaft 46 to displace the reducing member 50 about pivot axis 16.

Referring now to FIGS. 5-8, a method employing reducing instrument 10 will be discussed. Bone anchor 104 is shown removed from engagement with a bone structure, it being understood that bone anchor 104 could be engaged to any portion of any vertebra of a spinal column including the sacral, lumbar, cervical and/or thoracic regions. Elongate implant element 106 is provided with a length positionable between at least two vertebrae, and is shown adjacent to but spaced from bone anchor 104. Implant element 106 can be engaged to one or more other bone anchors prior to engagement with bone anchor 104. The anatomical structures and imprecise alignment between multiple bone anchors 104 can make positioning implant element into each of the bone anchors 104 difficult, particularly if implant element 106 includes a rigid or semi-rigid structure.

In the illustrated embodiment, bone anchor 104 is a side-loading type bone anchor with a distal bone engaging shaft 110 in the form a bone screw and a proximal head 112 defining a passageway 114 for receiving implant element 106 therethrough. The proximal head 112 can include a set screw or other suitable device for securing implant element 106 in the passageway 114 after it is positioned therein. Passageway 114 can open in the direction toward longitudinal axis 14 so that implant element 106 can be positioned therein when moved along lateral path 18.

Bone anchor 104 can further include a removable and proximally extending extension 130 extending from head 112. Extension 130 can include an elongated body 132 with a distal engaging end 134 removably and clampingly engaged to head portion 112 of bone anchor 104. Body 132 can also include a proximal end 136 sized to receive mounting member 20 thereover in sliding and removable engagement therewith. Mounting member 20 can be axially secured to extension 130 with any suitable means, including one or more set screws, clamping members, threaded interfaces, bayonet or twist locks, for example.

In one embodiment, extension 24 can include a quick disconnect type mechanism that axially secures mounting member 20 to extension 130. For example, extension 24 can include an inner sleeve and an outer sleeve axially biased relative to one another, and a number of ball members between the sleeves biased radially inwardly toward passage 32 when contacted by the outer sleeve but retained between the sleeves by the inner sleeve. The ball members can be unlocked by lifting the outer sleeve relative to the inner sleeve to axially displace the sleeves relative to one another, aligning a receptacle in the outer sleeve relative to the ball members so that the ball members can move away from passage 32 when contacted by an object in passage 32. Proximal end 136 is then free to slide into passage 32 to the desired depth without interference from the ball members. The outer sleeve can then be released to return to its normally biased position, contacting the ball members and forcing the ball members into passage 32 and into contact with proximal end 136 of extension 130 to provide an axially secure engagement relationship therewith. Proximal end 136 can include a flange, receptacle or other structure to provide positive axial engagement with the ball members or retained by a friction fit.

In any embodiment, extension 130 can be secured to bone anchor 104 prior to attachment of mounting member 20 to extension 130. Alternatively, mounting member 20 can be secured first to the extension 130, and the instrument assembly mounted to the bone anchor 104 as shown in FIG. 5.

Lateral displacement member 40 is situated relative to reducing member 50 so that reducing member 50 can freely pivot about axis 16 to align legs 54 with implant element 106. Once aligned, manipulation portion 80 can be distally displaced by rotating shaft 64 with handle 66, moving legs 54 distally along rails 68 until contact with implant element 106 is attained. Alternatively, push button 79 can be depressed to disengage quick-release mechanism 78 from shaft 64 so that manipulation portion 80 can axially and distally slide or translate relative to housing portion 52 into contact with implant element 106. Once contact with implant element 106 is achieved, button 79 is released and shaft 64 is re-engaged to allow displacement of shaft 64 and legs 54 by rotation of handle 66.

Figures 5, 6:
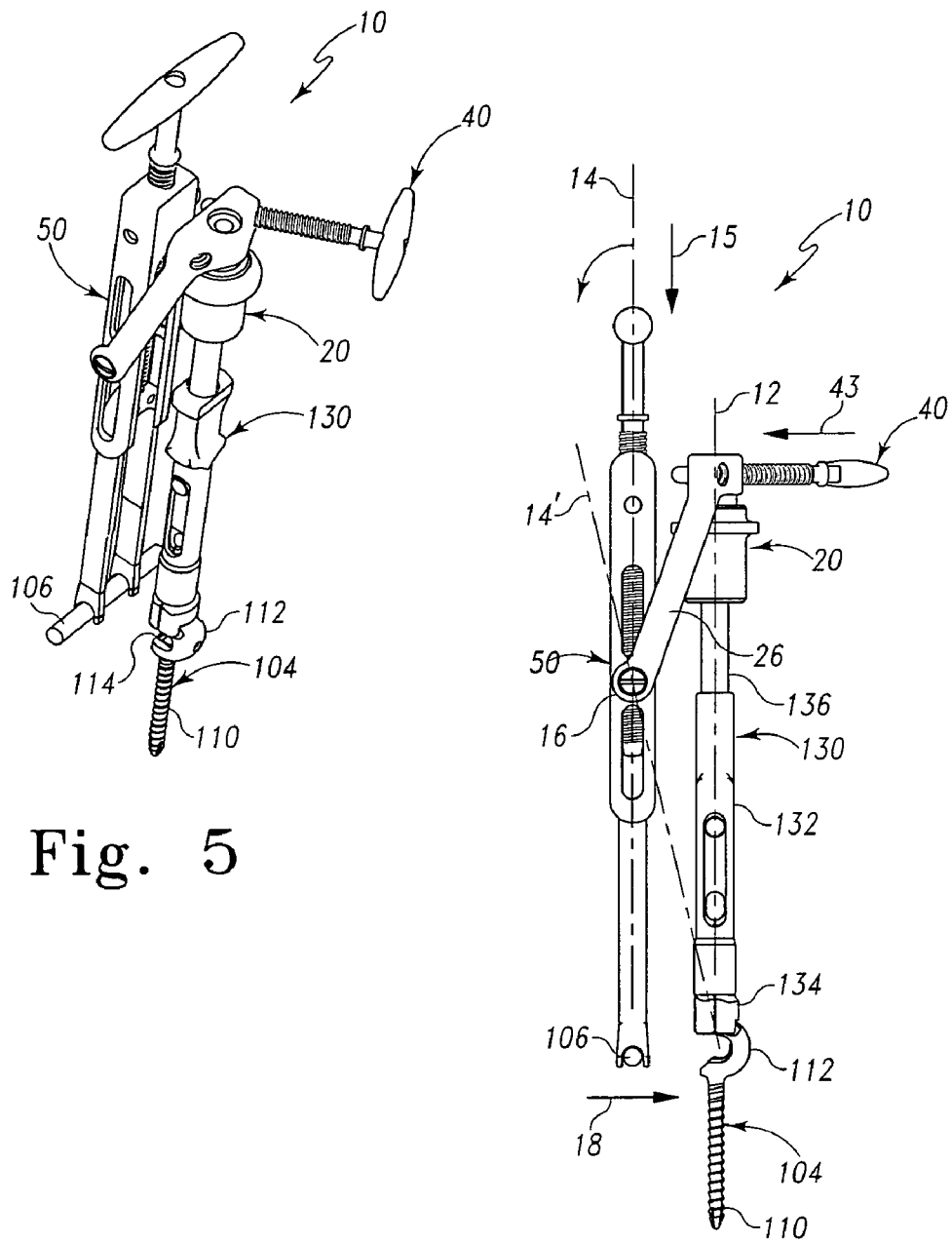
FIG. 5 is a perspective view showing an assembly including the surgical instrument of FIG. 2 mounted to an extension extending from an anchor and further with the surgical instrument engaged to an implant.
FIG. 6 is an elevation view of the assembly of FIG. 5 showing reduction of the implant element toward the bone anchor.
Figure 7:
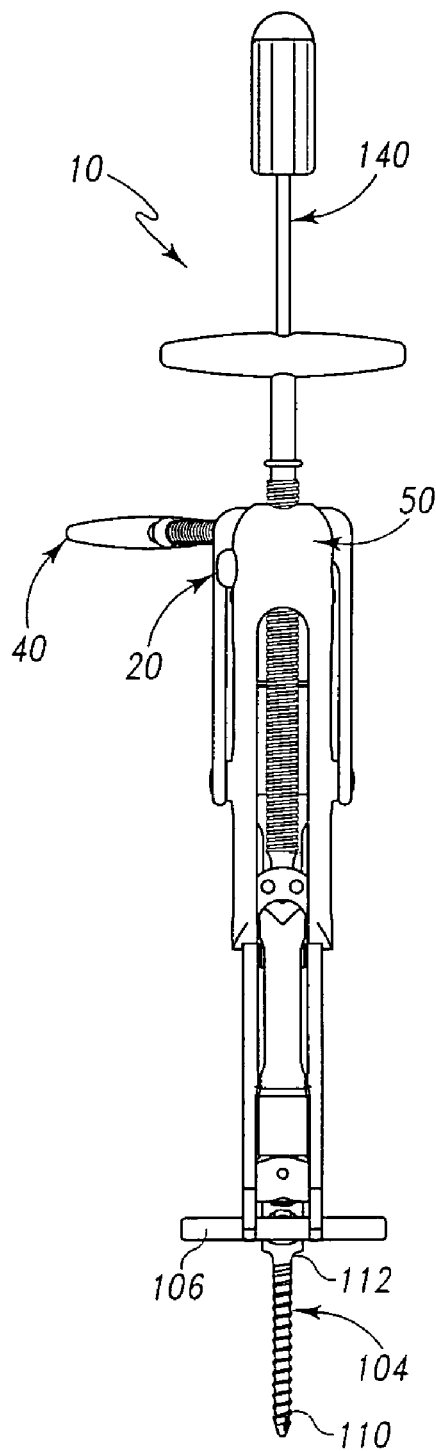
FIG. 7 is a side view showing the assembly and the implant element reduced into the bone anchor and a driving instrument positioned to secure the implant element in the bone anchor.
Figure 8:
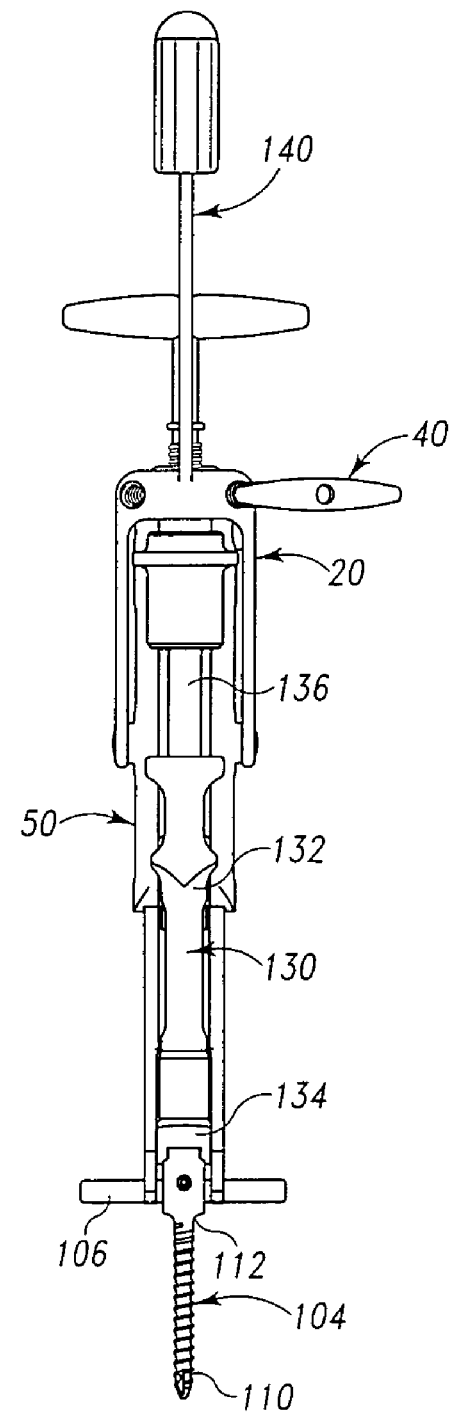
FIG. 8 is a side view looking in the direction opposite the direction of FIG. 7 showing the implant element reduced into the bone anchor and the driving instrument positioned to secure the implant element in the bone anchor.

Manipulation portion 80 can then be axially displaced while in contact with implant element 106, if necessary, to distally displace implant element 106 along axis 14 as indicated by arrow 15 in FIG. 6. Once implant element 106 is aligned or nearly aligned with the side opening into passageway 114 of head portion 112, lateral displacement member 40 is manipulated with handle 44 to position contact end 48 in contact with housing portion 52 and rotate reducing member 50 about pivot axis 16. This in turn displaces implant element 106 along path 18 toward head portion 112. If implant element 106 is not aligned sufficiently distally or proximally with the opening into passageway 114, handle 66 can be rotated to distally or proximally displace manipulation portion 80 to provide fine tuning of the location of implant element 106 relative to passageway 114. When the desired alignment is achieved, lateral displacement member 40 can be further operated to position and seat implant element 106 in passageway 114 as shown in FIGS. 7 and 8.

When implant element 106 is seated in head portion 112, legs 54 are positioned on opposite sides of head portion 112 and maintain implant element 106 in position through the engagement of lateral displacement member 40 with housing portion 52 and engagement of drive member 62 to housing portion 52. A driver instrument 140 can be positioned through passage 32 and through an internal passage of extension 130 to engage a set screw or other locking device on head portion 112. Driver instrument 140 can be rotated to rotate the locking device and finally engage implant element 106 in head portion 112. Reducing instrument 10 can then be removed by either disengaging extension 130 from bone anchor 104, or by disengaging mounting member 20 from extensions 130. The procedure can be repeated at various anchor locations if necessary or desirable to secure implant element 106 or another implant element to one or more other anchors along the spinal column.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Further, when the language "at least a portion" and/or "a portion" is used, the claims may include a portion and/or the entire item unless specifically stated to the contrary.

What is claimed is:

1. A surgical instrument to position an implant element relative to a bone anchor of a spinal implant system, comprising:

an elongated extension with a distal end removably engageable to the bone anchor and extending along a first longitudinal axis from said distal end to a proximal end;

a mounting member removably mountable to said proximal end of said extension along said first longitudinal axis, wherein said mounting member includes first and second linking arms extending distally from a proximal end of said mounting member;

a reducing member extending along a second longitudinal axis, said reducing member being pivotally linked to said mounting member in side-by-side relation about a pivot axis, said reducing member including at least one leg movable distally along said second longitudinal axis for positioning in contact with the implant element, wherein said first and second linking arms include distal ends coupled to opposite sides of said reducing member at said pivot axis and said first and second linking arms extend proximally from said distal ends in an oblique orientation to said first and second longitudinal axes to said proximal end of said mounting member when said first and second longitudinal axes are positioned in parallel relation to one another; and a lateral displacement member engaged to one of said mounting member and said reducing member and having a spaced position from a proximal portion of the other of said mounting member and said reducing member, said lateral displacement member being movable from said spaced position into contact with said proximal portion of said other of said mounting member and said reducing member while engaged to said one of said mounting member and said reducing member to move said proximal portion of said reducing member away from said mounting member about said pivot axis and to move a distal end of said at least one leg toward said distal end of said extension thereby positioning the implant element in a location more proximate the bone anchor.

2. The instrument of claim 1, wherein said mounting member includes a proximal head portion and a cylindrical extension extending distally from said head portion, said head portion and said extension defining a passage therethrough along said first longitudinal axis.

3. The instrument of claim 2, wherein said head portion includes a bore extending therethrough transversely to said first longitudinal axis, and said lateral displacement member extends through said bore in threaded engagement with said mounting member therein.

4. The instrument of claim 3, wherein said lateral displacement member includes a first end positionable in contact with said reducing member and an opposite end including a handle, said lateral displacement member further including an elongated shaft extending between said first end and said handle.

5. The instrument of claim 4, wherein said bore extends along a third axis that is obliquely oriented to a plane that is defined by said first and second longitudinal axes.

6. The instrument of claim 1, wherein said reducing member includes:

an elongated housing portion including a body defining a cavity along said second longitudinal axis; and a manipulation portion extending through said housing portion, said manipulation portion including a handle proximal of said housing and a pair of legs extending distally from said housing portion for contact with the implant element.

7. The instrument of claim 6, further comprising an elongated shaft between said handle and said pair of legs, wherein said pair of legs are joined at proximal ends thereof with a connector and a distal end of said shaft is rotatably engaged to said connector.

8. The instrument of claim 7, wherein said elongated shaft includes an external thread profile and is threadingly engaged to said housing portion, wherein rotation of said elongated shaft with said handle axially and rotationally displaces said shaft along said second longitudinal axis, which in turn axially and linearly displaces said pair of legs along said second longitudinal axis.

9. The instrument of claim 6, wherein said pair of legs each include a distal end with a concavely curved distal end surface for contacting the implant element when the implant element is positioned between the pair of legs.

10. The instrument of claim 6, wherein said housing portion includes a pair of rails extending distally therealong and said pair of legs are slidably received in grooves along facing sides of said pair of rails.

11. A surgical instrument to position implants relative to a bone anchor of a spinal implant system, comprising:
an elongated implant element;
a mounting member removably mountable to the bone anchor along a first longitudinal axis, said mounting member including at least one linking arm extending therefrom to a pivot end in an oblique orientation to said first longitudinal axis;
a reducing member extending along a second longitudinal axis adjacent said mounting member, said reducing member including a housing portion and a manipulation portion mounted to and movable relative to said housing portion, said housing portion being pivotally coupled to said pivot end of said linking arm about a pivot axis with said at least one linking arm obliquely oriented to said second longitudinal axis and with said at least one linking arm extending in a proximal direction away from the bone anchor to a proximal end of said mounting member, and said manipulation portion includes at least one distally extending leg contacting said implant element, wherein said at least one leg is movable distally relative to said housing portion along said second longitudinal axis for moving said implant element along said second longitudinal axis and said reducing member is pivotal relative to said mounting member about said pivot axis to change an orientation of said first and second longitudinal axes relative to one another and move said implant element transversely to said first longitudinal axis; and
a lateral displacement member engaged to said mounting member, said lateral displacement member having a spaced position from said reducing member, said lateral displacement member being movable from said spaced position to contact said reducing member while said lateral displacement member is engaged to said mounting member to push a proximal end of said reducing member away from said mounting member about said pivot axis and move said implant element in contact with said distally extending leg toward said first longitudinal axis.

12. The instrument of claim 11, wherein said mounting member includes a bore extending therethrough transversely to said first longitudinal axis, said lateral displacement member extending through said bore and engaging said mounting member therein.

13. The instrument of claim 12, wherein said lateral displacement member includes a first end positionable in contact with said reducing member and an opposite end including a handle, said lateral displacement member further including an elongated shaft extending between said first end and said handle, said shaft including a thread profile threadingly engaging said mounting member in said bore.

14. The instrument of claim 12, wherein said bore extends along a third axis that is obliquely oriented to a plane that is defined by said first and second longitudinal axes.

15. The instrument of claim 11, further comprising an elongated extension with a distal end removably engageable to the bone anchor and body extending along said first longitudinal axis to a proximal end removably engageable with said mounting member.

16. The instrument of claim 11, wherein said at least one linking arm includes a pair of linking arms pivotally coupled to opposite sides of said housing portion at said pivot axis.

17. The instrument of claim 11, wherein said at least one leg of said manipulation portion includes a pair of legs extending in side-by-side and spaced relation to one another, each of said pair of legs defining a concavely curved distal end and said implant element is positioned between said pair of legs in said concavely curved distal ends.

18. The instrument of claim 17, wherein said manipulation portion further comprises an elongated shaft between a proximal handle and said pair of legs, wherein said pair of legs are joined at proximal ends thereof with a connector and a distal end of said shaft is rotatably engaged to said connector.

19. The instrument of claim 18, wherein said elongated shaft includes an external thread profile and is threadingly engaged to said housing portion between said proximal handle and said distal end of said shaft, wherein rotation of said elongated shaft with said handle axially and rotationally displaces said shaft along said second longitudinal axis, which in turn axially and linearly displaces said pair of legs along said second longitudinal axis.

20. The instrument of claim 17, wherein said housing portion includes a pair of rails extending distally therealong and said pair of legs are slidably received in grooves along facing sides of said pair of rails.

\* \* \* \* \*